United States Patent [19]
Gudehus et al.

[11] Patent Number: 5,148,710
[45] Date of Patent: Sep. 22, 1992

[54] METHOD AND APPARATUS FOR DETERMINING THE RELATIVE HUMIDITY OF GASEOUS MATERIALS

[76] Inventors: Hans C. Gudehus, Power Weg 21, D-4513 Belm; Josef Ellmann, Moltkestrasse 8, D-4500 Osnabrueck; Edgar Bauth, Siedlung am Schwegermoor 1 A, D-4508 Bohmte-Hunteburg, all of Fed. Rep. of Germany

[21] Appl. No.: 660,602

[22] Filed: Feb. 25, 1991

[30] Foreign Application Priority Data

Feb. 23, 1990 [DE] Fed. Rep. of Germany ....... 4005744

[51] Int. Cl.$^5$ ............................................. G01N 25/68
[52] U.S. Cl. ..................................... 73/335.06; 374/20
[58] Field of Search .................... 73/29.01, 338, 336.5, 73/77; 374/20

[56] References Cited

U.S. PATENT DOCUMENTS

| | | | |
|---|---|---|---|
| 3,712,140 | 1/1973 | Grasso et al. | 73/338 |
| 4,227,411 | 10/1980 | Abramovich | 73/29.01 X |
| 4,279,150 | 7/1981 | Land | 73/338 |
| 4,629,333 | 12/1986 | Dosoretz et al. | 374/20 |

FOREIGN PATENT DOCUMENTS 265151 11/1988 Japan ................................. 73/29.01

Primary Examiner—Hezron E. Williams
Assistant Examiner—Joseph W. Roskos
Attorney, Agent, or Firm—Jordan and Hamburg

[57] ABSTRACT

A method for determining the relative humidity of gaseous materials, preferably for determining the relative humidity of air in rooms, such as greenhouses, whereby, using psychrometric moisture measurement, the temperature of the stream of gas, the relative humidity of which is to be measured, is determined by means of temperature sensors. A gas stream acting upon a moistenable wet temperature sensor is cooled up to a cooling limit (wet-bulb point) and the wet bulb point temperature is determined. The relative humidity is ascertained using the measured temperature of the gas and the wet-bulb temperature. In order to be able to carry out a reliable determination of the relative humidity over longer periods of time even in a high humidity range, the stream of gas, the humidity of which is to be measured, is initially cooled to at least its dew point temperature in order to moisten the wet temperature sensor directly, the dew point temperature is determined and the wet temperature sensor is moistened to a determinable extent with condensate condensing from the gas stream. After this, for determining the wet-bulb point temperature, the stream of gas is cooled adiabatically with evaporation of the condensate condensed on the wet temperature sensor.

19 Claims, 2 Drawing Sheets a)

b)

c)

METHOD AND APPARATUS FOR DETERMINING THE RELATIVE HUMIDITY OF GASEOUS MATERIALS

BACKGROUND OF THE INVENTION

The invention is directed to a method for determining the relative humidity of gaseous materials, perferably for determining the relative humidity of air in rooms, such as greenhouses, whereby, using psychrometric moisture measurement, the temperature of the stream of gas, the relative humidity of which is to be measured, is determined by means of a dry temperature sensor, which cools a gas stream acting upon a moistenable wet temperature sensor adiabatically up to the cooling limit (wet-bulb point) with determination of the wet bulb point temperature, and the relative humidity is ascertained using the measured temperature of the gas and the wet-bulb temperature. It is furthermore an object of the invention to provide an apparatus for carrying out a method for determining the relative humidity of gaseous materials in accordance with the introductory portion of claim 4.

The measurement and determination of the relative humidity of air is increasingly required for many different applications, for example, for controlling the heating and air-conditioning facilities in warehouses for the optimized warehousing of perishable goods, in medical facilities, such as operating rooms, in production buildings, for processing and handling hygroscopic materials, such as paper, textiles, tobacco or grain, but particularly in buildings, which are used for raising agricultural and also horticultural products. However, conditions, which create appreciable problems, exist in horticultural operations such as those conducted in greenhouses. For example, problems arise during the evening and night hours due to the radiation of heat or a lowering of the temperature, which result in an increase in the humidity of the air in the greenhouse. This increase in humidity leads to undesirable plant reactions, such as the bursting of buds, growth disorders, etc., when certain plant-specific limits are exceeded. The dropping of the temperature below the dew point also can also have particularly disadvantageous effects, since it furthers the massive occurrence of diseases, destructive insects, parasites and physiological disorders such as bud discoloration and can make it necessary, in a particular case, to use fungicides, which are expensive and not without risk. This makes it necessary to assign special importance to the climatic conditions.

Conventionally, the temperature of a horticultural production plant is controlled by alternately heating and venting. This is done party manually, but to an increasing degree by automatic means. However, this presupposes that, for controlling the temperature, methods and equipment for measuring the humidity are available, which are able to measure or determine the existing air humidity accurately and, moreover, also over longer periods of time and also in the high humidity range from 85 to 100% relative humidity.

Different methods are known, with the help of which the relative humidity can be determined. Equipment of the usual construction for measuring the humidity of air at the present time works according to the so-called evaporation method using the psychrometric measurement of humidity, which is based on the constant interchange of water vapor between water or ice and the surrounding atmosphere. In the case of the known equipment, which works according to this principle, the so-called psychrometers, a wet temperature sensor is provided with a textile sock, which is moistened from a water reservoir. The textile sock of the wet temperature sensor is disposed in the measuring chamber of the psychrometer and is acted upon by the air stream. In so doing, the air flowing past is cooled until it is saturated, that is, it is cooled up to the so-called wet-bulb point. This wet-bulb temperature is determined with the wet temperature sensor. The cooling up to the wet-bulb point should take place adiabatically, so that the heat of evaporation must be supplied exclusively by the air passing by. Accordingly, appropriate actions must be taken to ensure that heat is not supplied by the equipment itself, by radiation, from the water reservoir, etc.

The difference between the air temperature, which is determined with the dry temperature sensor, and the wet-bulb temperature is referred to as the psychrometric difference. The relative humidity can then be determined from an enthalpy/water content diagram (h-x diagram) with the help of the surrounding temperature and the wet-bulb point temperature. If modern data processing equipment is used, this can also be done by computer.

It is a disadvantage of psychrometers of the known construction that they cannot be used efficiently for measurements over long periods of time. The stocking must be wetted again at intervals of 10 to 15 minutes. Moreover, distilled water is required for the moistening, because the cotton stocking loses its absorptivity due to lime deposits and because salt deposits lower the vapor pressure. Before the measurement, the instruments must have been in the atmosphere that is to be measured long enough, so that their temperature matches that of the surroundings. If such instruments are to be used for continuous methods of measuring, as would be required, for example, by a modern heating and cooling control system in horticultural installations, limits are set. This is very disadvantageous, particularly for measurements in the high humidity range. In horticultural practice, where it is necessary to measure in the high humidity range, the effective control of the heating and cooling equipment with respect to controlling the temperature accurately therefore frequently fails to measure the air humidity accurately as a controlled variable over prolonged periods of time. This can be attributed to the unreliability or inaccuracy of such known instruments or their components.

SUMMARY OF THE INVENTION

It is therefore an object of the present invention to provide a method and an apparatus for determining the relative humidity of gaseous materials of the initially mentioned kind by employing psychrometric humidity measurements, with which the relative humidity can be determined accurately and effectively over longer periods of time even in the high humidity range of the relative humidity or with which the measurement data for determining the relative humidity can be measured reliably, in order to comply with the prerequisites for a modern, effective, automatic control system for cooling and heating.

For the inventive method, the psychrometric principle of measurement is retained within the restraints of a measurement cycle. The temperature of the gas is measured accurately at the dry temperature sensor and the wet-bulb temperature is measured accurately at the wet temperature sensor. For this purpose, however, the initially dry wet-temperature sensor is moistened by the stream of gas itself and therefore not by a supply of extraneous liquid. To accomplish this, the temperature sensor itself is cooled to begin with. This makes it possible to determine and hold the dew point temperature of the gas stream, so that it is available at the same time for determining and calculating the state data of the gas stream. The film of condensate, which moistens the wet temperature sensor directly, must be monitored in a manner, which is simple technologically and structurally. The film of condensate is monitored with respect to its thickness and, with that, with respect to the amount of condensate by means of, for example, an infrared radiation unit with integrated detector, so that the contact surface of the temperature surface likewise functions as an absorption surface. The absorption signal of such an infrared radiation unit can then be used to control the cooling process of the wet temperature sensor. For this purpose, it is advisable to pass first of all through the dew point, in order to have present the necessary thickness of liquid layer condensed from the gas stream and to fix the range of air humidity. In the case of a high humidity from 85 to 100%, the adiabatic state can be approached accurately for the purpose of determining the wet-bulb temperature precisely by way of a virtual thermal decoupling of, for example, a Peltier block as a cooling device with determination of the temperature of the hot side of the Peltier block and, when the steady state (stable equilibrium) is reached, this state can be measured accurately with a constant temperature course. In all other ranges, the dew point can also be used, in addition to the determination of the humidity of the air, as an auxiliary variable.

Using process control computers, the inventive method and the inventive apparatus make it possible, with discontinuous psychrometric measurement of the humidity of the air, to calculate the humidity of the air, as well as other important state variables of the air with an exceptionally high accuracy even over long periods of time, so that the prerequisites are created for using the relative humidity of the air as a reliable, controlled variable for regulating the temperature and humidity of, for example, a greenhouse by means of a process control computer.

The apparatus, intended for the implementation of the method, is equipped with only a small number of components. Should the temperature sensor become contaminated, for example, by deposits, then this can be recognized by a microprocessor, which can be provided for the signal processing and by means of which the cleaning processes in the instrument itself are initiated in that a cleaning condensate is deposited from the stream of gas onto the contact surface.

For further explanations, reference is made to the description and the drawings that follow. In the latter, the following is shown.

DESCRIPTION OF THE PREFERRED EMBODIMENTS

Figure 1:
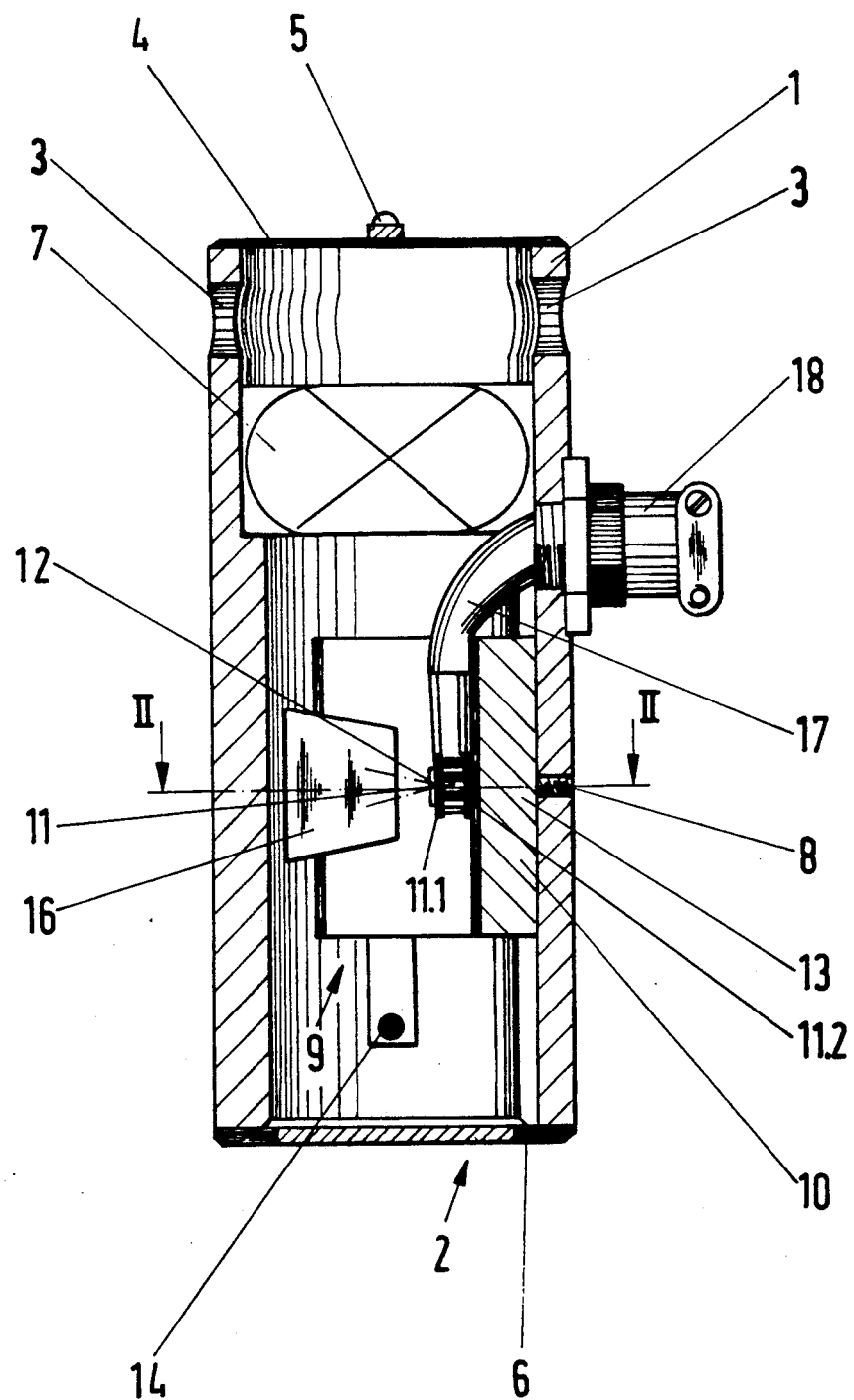
FIG. 1 shows a sectional side representation of an example of the operation of an inventive apparatus.

The inventive apparatus illustrated in the drawing shows a tubular measuring chamber 1, which is generally labelled 1, is protected against thermal radiation and is provided with an air inlet 2, as well as with air outlets 3. On the top side, the measuring chamber is closed off by a plate 4 and can be suspended by a hanger 5 at the desired height, for example, in a greenhouse.

The air inlet side is covered by a filter 6, which is permeable to gas and vapor. The interior of the measurement chamber is thus largely protected against the entry of dirt particles. In the interior of the measuring chamber, there is an axial blower 7, which can have an electrical driving mechanism, the details of which are not shown and which can be controlled by way of a central measuring and control unit. A measurement chamber insert 9 is mounted by means of a screw connection 8 with interposition of an adjusting spring 10 at the wall of the measurement chamber housing.

Figure 2:
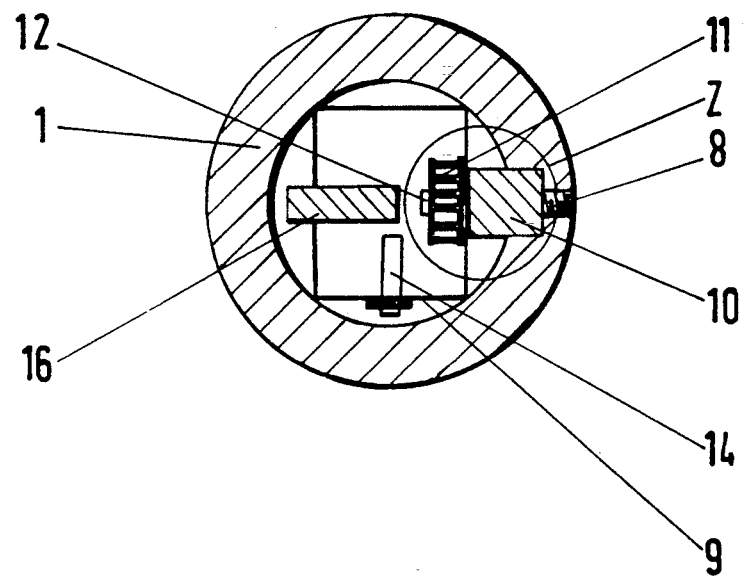
FIG. 2 shows a cross sectional representation along the line II—II in FIG. 1.
Figure 3:
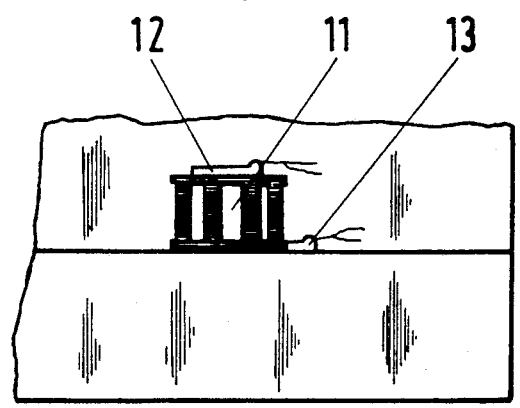
FIGS. 3a to 3c show a detail section Z from FIG. 2 on an enlarged scale of 2:1 in (a) a side view, (b) a front view and (c) a plan view.
Figure 3:
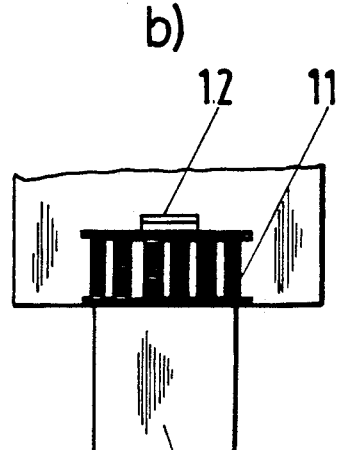
Figure 3:
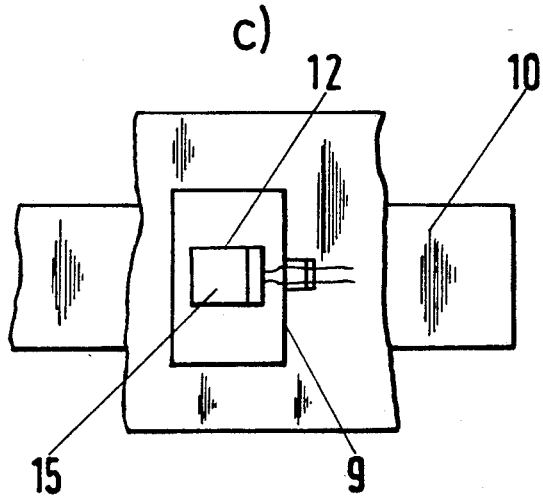

The measurement chamber insert is constructed as a square hollow profile (FIG. 2), with an air inlet and an air outlet, through which a gaseous material can flow. In its interior, a Peltier block 11 of known construction is disposed. On the cold side 11.1 of the Peltier block 11, a thin-film platinum thermometer, which forms the wet temperature sensor 12 (FIG. 3), is bonded with a heat-conductive adhesive. The hot side 11.2 faces the adjusting spring 10. It is, moreover, provided with a temperature resistance 13 for determining temperature of the Peltier block on the hot side.

The dry temperature sensor 14 for measuring the air inlet temperature is disposed ahead of the air inlet of the measurement chamber insert 9. The thin-film thermometer, which forms the wet temperature sensor 12, has a contact surface, which is labelled 15 (FIG. 3c) and likewise forms an infrared absorption surface. Opposite to the wet temperature sensor 12 in the measurement chamber insert 9, there is disposed an infrared measurement unit 16 with an infrared radiator and an infrared detector, so that the amount of condensate resulting on the contact surface can be determined by means of the infrared absorption. The Peltier block 11, wet temperature sensor 12, temperature resistance 13, dry temperature sensor 14 and infrared measuring unit 16 are connected over a connecting cable shaft 17 at a connecting outlet 18 with an electrical measuring and controlling unit, which is not shown; they are also energized by means of this unit, so that the measurement signals, which are ascertained, can be processed and, moreover, can also be utilized for controlling, for example, the cooling process or for the virtual thermal decoupling by determining the temperature of the hot side of the Peltier block 11 for the purpose of heading for an exact adiabatic state when determining the wet-bulb temperature.

For a measurement cycle with the apparatus shown in the drawing, first of all the temperature of the entering air stream is determined by means of the dry temperature thermometer 14 and stored in the unit, which controls the apparatus and processes the measured values. By means of the Peltier block 11, the thin-film platinum thermometer of the wet temperature sensor 12, which is bonded with the heat conducting adhesive and forms a wet temperature resistance, is cooled from room temperature to a convenient temperature below the dew point of the air stream. Once the dew point temperature is reached, the water is deposited as condensate on the surface of the contact area 15. This condensation is detected by the infrared absorption measurement unit 15 and likewise passed on as a measurement signal to the control and measurement unit. A condensate film of a determinable thickness is now provided on the contact surface 15. Due to the thermally conductive connection between the Peltier block 11 and the measurement chamber insert 9, the adjusting spring 10 and the housing 1 of the measurement chamber, the heat turning up during the cooling process on the hot side 11.2 of the Peltier block 11 is dissipated constantly over an adequately dimensioned body, which additionally is ventilated by an axial blower 7. The air in the vicinity of the wet temperature sensor 12 therefore generally cannot have a falsifying effect on the values measured. If necessary, the hot side of the Peltier block 11 can be insulated from the surface of the wet temperature sensor 12, around which the air is flowing.

Depending on the absolute amount of condensate, which can be condensed as a function of the absolute water content of the surrounding or process air and of the temperature below the dew point that can actually be achieved at the wet temperature sensor during the cooling process, the Peltier block 11 remains at the minimum temperature achievable at the wet temperature sensor 12, until sufficient condensate has been deposited in the form of dew or hoar at this sensor, in order to pass through an adiabatic cooling curve up to the wet-bulb point. This is checked continuously by the measurement and control unit.

After reaching an amount of condensate sufficient for heading for the wet-bulb point, the temperature on the hot side 11.2 of the Peltier block 11 and that of the wet temperature sensor 12 are determined continuously in a subsequent warming-up phase. From the difference between the temperatures, the measurement and control unit can calculate an energizing current to the Peltier block 11, so that the Peltier block 11 can be controlled with a control current, which guarantees that almost ideal adiabatic cooling is accurately maintained by the therewith realized virtual thermal decoupling of the hot and cold sides of the Peltier block. Such factors as the thermal conductivity of the Peltier block with the component constants, the temperature of the hot side of the Peltier block 11, the temperature of the cold side of the Peltier block 11 and the differentiated cold-side temperature can serve as parameters for the computing process in the control and measuring unit.

During the whole of the measuring cycle, air is passed through the interior of the measuring chamber with a flow velocity, which is adapted to the conditions and usually amounts to 2.5 to 3 m/sec. The air flowing past the moistened wet temperature sensor 12 supplies the amount of heat, which is required in order to permit the condensed water to evaporate again as a function of the saturation deficiency of the air. The air passing by, cooled by evaporation of the previously thawed condensate, favors through the controlled cooling process (virtual thermal decoupling) a stable state of equilibrium, which ensures that the relative humidity can be calculated precisely by way of measuring the wet-bulb temperature.

If the measuring and control unit recognizes, for example, because of the cooling curve determined for the wet temperature sensor, that there is no longer any condensed water on the contact surface 15, then either the surrounding conditions lie outside of the cooling capacity of the Peltier block 11 or the contact surface is highly contaminated. In this case, an automatic cleaning process can be carried out simply by forming an excess of condensed water and subsequently heating. The arrangement of the wet temperature sensor 12 ensures that the excess condensate, which contains the impurities, can drip off unimpededly. The development of algae is thus also prevented.

What is claimed is:

1. A method of determining the relative humidity of a gaseous medium comprising the steps of passing a stream of gaseous medium of which the relative humidity is to be determined to a measuring passage, providing a moistenable wet temperature sensor in said measuring passage, cooling said moistenable wet temperature sensor below the dew point temperature of said gaseous medium, condensing moisture in said gaseous medium on said moistenable wet temperture sensor, determining the thickness of the film of condensate on said moistenable wet temperature sensor, measuring the wet bulb temperature at said moistenable wet temperature sensor, providing a dry temperature sensor, measuring the dry temperature of said dry temperature sensor, and utilizing said measured temperatures for determining the relative humidity of said gaseous medium.

2. A method according to claim 1 further comprising determining the thickness of said film of condensate utilizing infrared absorption.

3. A method according to claim 1, wherein said step of determining said thickness of said film of condensate comprises feeding a signal representing said thickness to an electrical control unit.

4. A method according to claim 3, wherein said step of measuring said wet bulb temperature comprises feeding a signal representing said wet bulb temperature to said electrical control unit, said step of measuring said dry temperature comprising feeding a signal representing said dry temperature to said electrical control unit.

5. A method according to claim 1, wherein said step of cooling said moistenable wet temperature sensor comprises utilizing a Peltier block.

6. A method according to claim 5 further comprising utilizing the temperature of the hot side of said Peltier block to control the cooling of said moistenable wet temperature sensor.

7. A method according to claim 5, wherein said step of utilizing a Peltier block comprises disposing said moistenable wet temperature sensor on the cold side of said Peltier block.

8. A method of determining the relative humidity of a gaseous medium comprising the steps of passing a stream of gaseous medium of which the relative humidity is to be determined to a measuring passage, providing a moistenable wet temperature sensor in said measuring passage, cooling said moistenable wet temperature sensor below the dew point temperature of said gaseous medium, condensing moisture in said gaseous medium on said moistenable wet temperature sensor, maintaining a film of condensate of predetermined thickness on said moistenable wet temperature sensor, measuring the wet bulb temperature at said moistenable wet temperature sensor, providing a dry temperature sensor, measuring the dry temperature of said dry temperature sensor, and utilizing said measured temperatures for determining the relative humidity of said gaseous medium.

9. A method according to claim 8 further comprising determining the thickness of said film of condensate using an infrared measuring unit.

10. A method according to claim 9 further comprising utilizing the measured value of said infrared measuring unit to control the extent of condensate on said moistenable wet temperature sensor so as to provide an amount of condensate on said moistenable wet temperature sensor which effects a cleaning action on said moistenable wet temperature sensor.

11. Apparatus for determining the relative humidity of a gaseous medium comprising a passage means through which a stream of said gaseous medium passes, a moistenable wet temperature sensor disposed in said passage means, Peltier block means for cooling said moistenable wet temperature sensor such that moisture in said gaseous medium is condensed on said moistenable wet temperature sensor, said moistenable wet temperature sensor comprising a film sensor element affixed to said Peltier block means, thermally conductive adhesive means for affixing said moistenable wet temperature sensor to said Peltier block means, a dry temperature sensor for sensing the dry temperature of said stream of gaseous medium, electric connection means connecting said moistenable wet temperature sensor, said Peltier block means, and said dry temperature sensor such that said electrical connecting means receives signals representing the wet bulb temperature from said moistenable wet temperature sensor and signals representing the dry temperature from said dry temperature sensor to thereby determine the relative humidity of said gaseous medium.

12. Apparatus according to claim 11 further comprising a blower means in said passage means for blowing said stream of gaseous medium through said passage means, said blower means being disposed downstream of said moistenable wet temperature sensor and downstream of said dry temperature sensor.

13. Apparatus according to claim 12, wherein said blower means comprises a blower and control means for controlling the operation of said blower.

14. Apparatus according to claim 11 further comprising a filter means permeable to gas and vapor disposed on said passage means.

15. Apparatus according to claim 11, wherein said moistenable wet temperature sensor senses the wet bulb temperature and said dry temperature sensor senses the dry bulb temperature, said electrical control means receiving signals from said moistenable wet temperature sensor and said dry sensor and determining the wet bulb temperature and the dry bulb temperature and utilizing said wet bulb temperature and dry bulb temperature to determine the relative humidity of said gaseous medium.

16. Apparatus for determining the relative humidity of a gaseous medium comprising a passage means through which a stream of said gaseous medium passes, a moistenable wet temperature sensor disposed in said passage means, Peltier block means for cooling said moistenable wet temperature sensor such that moisture in said gaseous medium is condensed on said moistenable wet temperature sensor, thermally conductive connecting means connecting said Peltier block means to said passage means, a dry temperature sensor for sensing the dry temperature of said stream of gaseous medium, electric connection means connecting said moistenable wet temperature sensor, said Peltier block means, and said dry temperature sensor such that said electrical connecting means receives signals representing the wet bulb temperature from said moistenable wet temperature sensor and signals representing the dry temperature from said dry temperature sensor to thereby determine the relative humidity of said gaseous medium.

17. Apparatus for determining the relative humidity of a gaseous medium comprising a passage means through which a stream of said gaseous medium passes, a moistenable wet temperature sensor disposed in said passage means, Peltier block means for cooling said moistenable wet temperature sensor such that moisture in said gaseous medium is condensed on said moistenable wet temperature sensor, infrared absorption means on said moistenable wet temperature sensor, an infrared measuring means disposed in said passage means operable with said infrared absorption means for determining the extent of moisture on said moistenable wet temperature sensor, a dry temperature sensor for sensing the dry temperature of said stream of gaseous medium, electric connection means connecting said moistenable wet temperature sensor, said Peltier block means, and said dry temperature sensor such that said electrical connecting means receives signals representing the wet bulb temperature from said moistenable wet temperature sensor and signals representing the dry temperature from said dry temperature sensor to thereby determine the relative humidity of said gaseous medium.

18. Apparatus for determining the relative humidity of a gaseous medium comprising a passage means through which a stream of said gaseous medium passes, a moistenable wet temperature sensor disposed in said passage means, Peltier block means for cooling said moistenable wet temperature sensor such that moisture in said gaseous medium is condensed on said moistenable wet temperature sensor, a temperature resistance means disposed on the hot side of said Peltier block means for determining the temperature of said hot side, a dry temperature sensor for sensing the dry temperature of said stream of gaseous medium, electric connection means connecting said moistenable wet temperature sensor, said Peltier block means, and said dry temperature sensor such that said electrical connecting means receives signals representing the wet bulb temperature from said moistenable wet temperature sensor and signals representing the dry temperature from said dry temperature sensor to thereby determine the relative humidity of said gaseous medium.

19. Apparatus for determining the relative humidity of a gaseous medium comprising a passage means through which a stream of said gaseous medium passes, a moistenable wet temperature sensor disposed in said passage means, Peltier block means for cooling said moistenable wet temperature sensor such that moisture in said gaseous medium is condensed on said moistenable wet temperature sensor, a dry temperature sensor for sensing the dry temperature of said stream of gaseous medium, a measurement chamber means disposed in said passage means, said gaseous medium passing through said measurement chamber means, said moistenable wet temperature sensor being disposed in said measurement chamber means, said dry temperature sensor being disposed in said passage means upstream of said measurement chamber means, an infrared measurement means on said measurement chamber means operable to detect the extent of moisture on said moistenable wet temperature sensor, electric connection means connecting said moistenable wet temperature sensor, said Peltier block means, and said dry temperature sensor such that said electrical connecting means receives signals representing the wet bulb temperature from said moistenable wet temperature sensor and signals representing the dry temperature from said dry temperature sensor to thereby determine the relative humidity of said gaseous medium.

* * * * *